(12) United States Patent
Linz et al.

(10) Patent No.: US 8,188,086 B2
(45) Date of Patent: May 29, 2012

(54) SPECIFIC SALT, ANHYDROUS AND CRYSTALLINE FORM OF A DIHYDROPTERIDIONE DERIVATIVE

(75) Inventors: Guenter Linz, Mittelbiberach (DE); Peter Sieger, Mittelbiberach (DE); Matthias Grauert, Biberach (DE); Rolf Schmid, Baltringen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/212,188

(22) Filed: Sep. 17, 2008

(65) Prior Publication Data

US 2009/0030004 A1    Jan. 29, 2009

Related U.S. Application Data

(63) Continuation of application No. 11/668,681, filed on Jan. 30, 2007, now Pat. No. 7,439,358.

(30) Foreign Application Priority Data

Feb. 8, 2006  (EP) ..................................... 06101414

(51) Int. Cl.
C07D 487/04 (2006.01)
A61K 31/4985 (2006.01)
A61P 35/00 (2006.01)

(52) U.S. Cl. .................................. 514/252.13; 544/256
(58) Field of Classification Search .................. 544/258; 514/249
See application file for complete search history.

(56) References Cited

U.S. PATENT DOCUMENTS

| 4,957,922 | A |   | 9/1990  | Lammens et al. |
|-----------|---|---|---------|----------------|
| 5,043,270 | A |   | 8/1991  | Abrams et al.  |
| 5,167,949 | A |   | 12/1992 | Ferrand et al. |
| 5,198,547 | A | * | 3/1993  | Bailey et al. ........... 544/258 |
| 5,424,311 | A |   | 6/1995  | Billhardt-Troughton et al. |
| 5,698,556 | A |   | 12/1997 | Chan |
| 6,096,924 | A |   | 8/2000  | Studer et al. |
| 6,156,766 | A | * | 12/2000 | Arita et al. .............. 514/300 |
| 6,174,895 | B1 |   | 1/2001 | Kleinman |
| 6,605,255 | B2 |   | 8/2003 | Kroll et al. |
| 6,806,272 | B2 |   | 10/2004 | Bauer et al. |
| 6,861,422 | B2 | * | 3/2005 | Hoffmann et al. ......... 514/228.5 |
| 6,875,868 | B2 |   | 4/2005 | Bonnert et al. |
| 7,238,807 | B2 |   | 7/2007 | Duran et al. |
| 7,241,889 | B2 |   | 7/2007 | Hoffmann et al. |
| 7,332,491 | B2 |   | 2/2008 | Grauert et al. |
| 7,371,753 | B2 |   | 5/2008 | Stadtmueller et al. |
| 7,414,053 | B2 |   | 8/2008 | Grauert et al. |
| 7,439,358 | B2 |   | 10/2008 | Linz et al. |
| 7,547,780 | B2 |   | 6/2009 | Grauert et al. |
| 7,625,899 | B2 |   | 12/2009 | Hoffmann et al. |
| 7,626,019 | B2 |   | 12/2009 | Duran et al. |
| 7,629,460 | B2 |   | 12/2009 | Grauert et al. |
| 7,723,517 | B2 |   | 5/2010 | Grauert et al. |
| 7,728,134 | B2 |   | 6/2010 | Linz et al. |
| 7,759,347 | B2 |   | 7/2010 | Hoffmann |
| 7,807,831 | B2 |   | 10/2010 | Grauert et al. |
| 7,816,530 | B2 |   | 10/2010 | Grauert |
| 8,003,786 | B2 |   | 8/2011 | Hoffmann et al. |
| 2002/0183292 | A1 |  | 12/2002 | Pairet et al. |
| 2002/0183293 | A1 |  | 12/2002 | Banerjee et al. |
| 2003/0130286 | A1 |  | 7/2003 | Denny et al. |
| 2004/0029885 | A1 |  | 2/2004 | Bauer et al. |
| 2004/0147524 | A1 |  | 7/2004 | Bauer et al. |
| 2004/0176380 | A1 |  | 9/2004 | Hoffmann et al. |
| 2005/0014760 | A1 |  | 1/2005 | Hoffmann et al. |
| 2005/0014761 | A1 |  | 1/2005 | Hoffmann et al. |
| 2005/0148501 | A1 |  | 7/2005 | Palmer et al. |
| 2005/0159414 | A1 |  | 7/2005 | Nickolaus et al. |
| 2005/0165010 | A1 |  | 7/2005 | Nickolaus et al. |
| 2006/0004014 | A1 |  | 1/2006 | Hoffmann et al. |
| 2006/0009457 | A1 |  | 1/2006 | Hoffmann et al. |
| 2006/0025411 | A1 |  | 2/2006 | Hoffmann et al. |
| 2006/0035902 | A1 |  | 2/2006 | Linz et al. |
| 2006/0035903 | A1 * | | 2/2006 | Mohr et al. .................. 514/251 |
| 2006/0046989 | A1 |  | 3/2006 | Grauert et al. |
| 2006/0047118 | A1 |  | 3/2006 | Stadtmueller et al. |
| 2006/0052383 | A1 |  | 3/2006 | Grauert et al. |
| 2006/0058311 | A1 |  | 3/2006 | Munzert et al. |
| 2006/0074088 | A1 |  | 4/2006 | Munzert et al. |
| 2006/0079503 | A1 |  | 4/2006 | Schwede et al. |
| 2007/0043055 | A1 |  | 2/2007 | Maier et al. |
| 2007/0208027 | A1 |  | 9/2007 | Duran et al. |

(Continued)

FOREIGN PATENT DOCUMENTS

CA        2458699 A1    3/2003

(Continued)

OTHER PUBLICATIONS

Liu, Rong, ed., Water-Insol. Drug Formul. (CRC Press, 2008) Ch. 15, pp. 417-435.*
Bastin et al., Org. Process Res. & Develop. 2000, 4, 427-435.*
Morris, et al., Intern'l. J. Pharma. 105 (1994) 209-217.*
Adeyeye, Moji, ed., Preformulation in Solid Dosage Form Development (Informa Healthcare, 2008) Ch. 2.3, pp. 63-80.*
Gould, Intern'l J. Therap. 33, 201 (1986).*
Serajuddin, Advan. Drug Deliv. Rev. 59 (2007) 603-616.*
Swarbrick et al., eds., Encyclopedia of Pharm. Tech. 13 (Marcel Dekker, NY 1996) pp. 453-499.*
XRD, X-Ray Diffraction Patterns, http://www.gly.uga.edu/Schroeder/geol6550/XRD.html , downloaded Mar. 9, 2011.*

(Continued)

*Primary Examiner* — James O Wilson
*Assistant Examiner* — Cecilia M Jaisle
(74) *Attorney, Agent, or Firm* — Michael P. Morris; Anthony P. Bottino

(57) ABSTRACT

The present invention relates to a specific salt of a dihydropteridione derivative, namely the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, to its crystallization in the form of an hydrate with water, to a process for the manufacture thereof, and to the use thereof in a pharmaceutical composition.

5 Claims, 3 Drawing Sheets

U.S. PATENT DOCUMENTS

| | | |
|---|---|---|
| 2007/0213528 A1 | 9/2007 | Duran et al. |
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0023733 A1 | 1/2009 | Cage et al. |
| 2009/0029990 A1 | 1/2009 | Maier et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |
| 2010/0280037 A1 | 11/2010 | Linz et al. |
| 2010/0324288 A1 | 12/2010 | Hoffmann et al. |

FOREIGN PATENT DOCUMENTS

| | | |
|---|---|---|
| CA | 2517010 A1 | 9/2004 |
| CA | 2517020 A1 | 9/2004 |
| CA | 2576290 A1 | 2/2006 |
| EP | 143478 A1 | 6/1985 |
| EP | 347146 A2 | 12/1989 |
| EP | 399856 A1 | 11/1990 |
| EP | 429149 A1 | 5/1991 |
| ES | 2287583 | 12/2007 |
| RU | 2002125451 A | 1/2004 |
| WO | 9609045 A1 | 3/1996 |
| WO | 9634867 A1 | 11/1996 |
| WO | 9636597 A1 | 11/1996 |
| WO | 9811893 A1 | 3/1998 |
| WO | 0119825 A1 | 3/2001 |
| WO | 0170741 A1 | 9/2001 |
| WO | 0178732 A1 | 10/2001 |
| WO | 02057261 A2 | 7/2002 |
| WO | 02076954 A1 | 10/2002 |
| WO | 02076985 A1 | 10/2002 |
| WO | 2003020722 A1 | 3/2003 |
| WO | 03093249 A1 | 11/2003 |
| WO | 2004014899 A1 | 2/2004 |
| WO | 2004076454 A1 | 9/2004 |
| WO | 2004093848 A2 | 11/2004 |
| WO | 2005067935 A1 | 7/2005 |
| WO | 2006/018221 A1 | 2/2006 |
| WO | 2006018182 A1 | 2/2006 |
| WO | 2006018185 A2 | 2/2006 |
| WO | 2006018220 A2 | 2/2006 |
| WO | 2006018221 A1 | 2/2006 |
| WO | 2006021378 A1 | 3/2006 |
| WO | 2007014838 A1 | 2/2007 |
| WO | 2007090844 A1 | 8/2007 |
| WO | 2009019205 A1 | 2/2009 |

OTHER PUBLICATIONS

GIRON; Thermal analysis and calorimetric methods in the characterisation of polymorphs and solates; Thermochimica Acta; No. 248; 1995; pp. 1-59.

International Search Report (PCT/ISA/206) for corresponding International Application PCT/EP2007/051139.

Voskoglou-Nomikos, T. et al., "Clinical predictive value of the in vitro cell line, human xenograft, and mouse allograft preclinical cancer models". Clinical Cancer Research vol. 9, 2003, pp. 4227-4239.

Wagner, G. et al., "Synthesis of new phrido[3',2':4,5] thieno '3,2-d 1,2,3-triazine derivatives as antianaphylactics". Biosciences Dept of the University of Leipzig, Pharmazie (Pharmacy), 48, 19923, vol. 7, pp. 514-518.

Webster's Comprehensive Dictionary, 1996, pp. 1013-1014.

Wolf, D. E.et al., "The structure of rhizopterin". Contribution from the Research Labs of Merck and Co. Inc. Nov. 1947, Journal of American Chem. Soc., vol. 69, pp. 2753-2759. XP002352205.

Chen, J.X. et al., "Parallel differentiated recognition of ketones and acetals". Angewandte Chemie Int. Ed, vol. 37, Issue 1/2, p. 91-93, 1998.

Jamieson, C. et al., "Application of ReactArray Robotics and Design of Experiments Techniques in Optimisation of Supported Reagent Chemistry". Org. Proc. Res. & Dev., 2002, 6, p. 823-825.

Mayer, SF, et al., "Enzyme-initiated domino (cascase) reactions". Chem. Soc. Rev, 2001, p. 332-339.

Science, vol. 310, Oct. 21, 2005, p. 409, Chemistry: One After Another.

Turner, S., "The Design of Organic Syntheses". Elsevier, 1976, pp. 10 and 149.

Wagner, B. et al, "7-Benzylamino-6-chloro-2-piperazino-4-pyrrolidino-pteridine, a potent inhibitor of cAMP—specific phosphodiesterase, enhancing nuclear protein binding to the CRE consensus sequence in human tumour cells", Biochemical Pharmacology, Pergamon, Oxford, GB, 2002, pp. 659-668.

Wikipedia. "Melting Point", Jan 17, 2007. http://en.wikipedia.org/wiki/Melting_point.

Berge, S. M., "Pharmaceutical Salts". Journal of Pharmaceutical Sciences, Jan. 1977, vol. 66, No. 1, p. 1-19.

Gould, P.I., "Salt selection for basic drugs". International Journal of Pharmaceuticals, 33, 1986, p. 201-217.

International Search Report for PCT/EP2005/056291 mailed Mar. 21, 2006.

McInnes, C. "Inhibitors of polo-like kinase reveal roles in spindle-pole maintenance". Nature Chemical Biology, vol. 2, No. 11, Nov. 2006, p. 608.

Neidle, S. ed., "Cancer Drug Design and Discovery", Elsevier/Academic Press, 2008, p. 427-431.

Steegmaier, M. et al. "BI 2536, a potent and selective inhibitor of polo-like kinase 1, inhibits tumor growth in vivo". Current Biology, 2007, 17(4), p. 316-322.

Stephenson, D.T. et al. "The effects of a selective dopamine D2 receptor agonist on behavioral and pathological outcome in 1-methl-4-phenyl-1,2,3,6-tetrahydropyridine—treated squirrel monkeys". J. Pharmacology and Experimental Therapeutics, vol. 303, No. 2, 2002, p. 1257.

Walsh, F. "No "Magic Bullet" Cure for Cancer". BBC News Feb. 1, 2007, http://news.bbc,co.uk/2/health/6310697.stm, downloaded Jul. 6, 2010.

Dyson, G, et al. "The Chemistry of Synthetic Drugs". 1964, p. 12-19.

Mashkovkii, M.D., "Medicaments". Moscow, Novaja Volna, 2001, vol. 1, p. 11.

Mashkovskii, M.D. "Drugs", Handbook for Doctors, 1993, Part I, Ch.1, p. 8.

Mikhailov, I.B., Principles of Rational Pharmacotherapy. Handbook for clinical pharmacology for students of pediatric and medical faculties of medical high schools, St. Petersburg, Russia, "Foliant", 1999, p. 25.

Kummer B, et al., "Combination of Radiation and Polo-like Kinase 1 Inhibition with BI6727 in tumour model A431". Vortrag. 20. Symposium •Experimentelle Strahlentherapie and klinische Strahlenbiologie, Exp. Strahlenther. Klin. Strahlenbiol. 20: 93-96 (2011) (Lecture 20, Symposium Experimental Radiation Therapy and Clinical Radiation Biology.)

Kummer, B. et al., Presentation: "Combination of irradiation and polo-like kinase 1 inhibition with BI 6727 in tumour model A 431". OncoRay—National Centre for Radiation Research in Oncology, Dresden 2011, Experimental Radiotherapy and Clinical Radiobiology.

Ahmad, N. "Polo-like kinase (Plk) 1: a novel target for the treatment of prostate cancer". Dept of Dermatology, Univ. Wisconsin, pp. 3-5.

BBC News/Health, Killer Breast Cancern Therapy Hope, www.newsvote.bbc/co./uk, downloaded Mar. 26, 2009.

Doerwald, F.Z. "Side reactions in organice synthesis". 2005.

Ferrand, G., et al., "Synthesis and potential antiallergic activity of new pteridinones and related compounds". Eur. J. Med. Chem, 31, 1996, pp. 273-280. XP-2246920.
Kimball, S. D. et al., "Cell cycle kinases and checkpoint regulation in cancer". Annual Reports in Medicinal Chemistry, 36, Chapter 14, pp. 139-148.
Leukemia & Lymphoma Society—Disease Information-Lymphoma. www.leukemia-lymphoma.org/all_page? item_id-7030, downloaded Mar. 26, 2009.
Leukemia & Lymphoma Society—Disease Information. www.leukemia-lymphoma.org/all_page?item_id-7026, downloaded Mar. 26, 2009.
MedlinePlus: Bacterial Infections. www.nim.nih.gov/medlineplus/print/bacterialinfections.htm, downloaded Mar. 26, 2009.
MedlinePlus: Viral Infections. www.nim.nih.gov/medlineplus/print/viralinfections.htm, downloaded Mar. 26, 2009.
National Kidney Foundation: Chronic Kidney Disease (CKD). www.kidney.org/kidneydisease/ckd/index.cfm, downloaded Mar. 26, 2009.
Norman, P. "PDE4 inhibitors". 1999, Ashley Publications Ltd., pp. 1101-1118.
Office Action mailed Dec. 10, 2003 for U.S. Appl. No. 10/226,710 filed Aug. 23, 2002.
Office Action mailed Apr. 28, 2004 for U.S. Appl. No. 10/374,876 filed Feb. 26, 2003.
Santing, R. E. et al., "Brochodilatory and anti-inflammatory properties of inhaled selective phosphodiesterase inhibitors in a guinea pig model of allergic asthma" European Journal of Pharmacology, 429, 2001, pp. 335-344.
Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.
Snyder, J. S. et al., "Common bacteria whose susceptibility to antimicrobials is no longer predictable". NCBI, PubMed, 2000, J. Med. Liban, 48, pp. 208-214.
Souillac, P. et al., "Characterization of delivery systems, differential scanning calorimetry". pp. 212-227, 1998.
Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21-pp. 129-133.
Viral Defense Foundation. www.viraldefense.org/mission.htm, downloaded Mar. 26, 2009.
Visiting Nurse Association of America. www.vnaa.org/gen/Germ_Protection_Center_Cold_and_Flu_Resources,html, downloaded Mar. 26, 2009.
ACPS Meeting, Background Information. "Scientific considerations of plymorphism in pharmaceutical solids: abbreviated new drug applications". Oct. 2002.
Ahlenius, T. List of cardiovascular disorder/diseases. Ahlenius, Karolinska Institutet. Stockholm, Sweden. Cardiovascular Diseases, p. 1-34, Apr. 2007.
Ahmad, N. "Polo-like kinase (Plk) 1: a novel target for the treatment of prostate cancer". The FASEB Journal. 2004, 18:5-7. Dept of Dermatology, Univ. Wisconsin, pp. 5-7.
Arnold, K. "Collaboration to play key role in NCI's future, director says". Journal of the National Cancer Institute, Jun. 5, 2002, pp. 790-792, vol. 94, No. 11.
BBC News/Health, Killer Breast Cancern Therapy Hope, www.newsvote.bbc/co./uk, Published Jan. 21, 2006.
Bennett, J.C., et al., "Textbook of Medicine", Part XIV, Oncology, 1997.
Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.
Dipolar aprotic solvent. Exhibit A, IUPAC Compendium of Chemical Terminology, 2nd Edition, 1997.
Doerwald, F.Z. Book Wiley-VCH Verlag GmbH & Co. KGaA, "Side reactions in organice synthesis: A Guide to Successful Synthesis Design". 2005.

Eurasian Opinion, Appln No. 2007/00389/28, Maly Slatoustinsky per., d.10, kv.15, 101000 Moscow, Russia, "EVROMARKPAT", 2007.
Ferrand, G., et al., "Synthesis and potential antiallergic activity of new pteridinones and related compounds". Eur. J. Med. Chem, 31, 1996, pp. 273-280. XP—2246920.
Ghandi, L., et al., "An Open-Label Phase II Trial of the PLK Inhibitor BI 2536 in Patients with Sensitive Relapse Small Cell Lung Cancer". ASCO Meeting 2009.
Goodman-Gilman's "The Pharmacological Basis of Therapeutics". Ninth edition, 1996, pp. 1225-1271.
Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.
Jaworska, J., et al., "Review of methods for assessing the applicability domains of SARS and QSARS". Sponsor: The European Commission—Joint Research Ctr., Institute for Health and Consumer Protection—ECVAM, Italy, 2004.
Kashima, M. K. et al., "Expression of polo-like kinase (PLK1) in non-Hodgkin's lymphomas". NCBI, PubMed, 2005.
Kimball, S. D. et al., "Cell cycle kinases and checkpoint regulation in cancer". Annual Reports in Medicinal Chemistry, 36, Chapter 14, 2001, pp. 139-148.
Leukemia & Lymphoma Society—Disease Information-Lymphoma. www.leukemia-lymphoma.org/all_page?item_id-7030, 2008.
Leukemia & Lymphoma Society—Disease Information. www.leukemia-lymphoma.org/all_page?item_id-7026, 2008.
Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.
Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.
MedlinePlus: Bacterial Infections. www.nim.nih.gov/medlineplus/print/bacterialinfections.htm, date last updated Mar. 25, 2009.
MedlinePlus: Viral Infections. www.nim.nih.gov/medlineplus/printiviralinfections.htm, date last updated Feb. 11, 2009.
Merck Manual of Medical Information—Home Edition, Section 17. "Parasitic Infections". Chapter 184, 2003.
Mito, K., et al., "Expression of polo-like kinase (PLK1) in non-Hodgkin's lymphomas". NCBI, PubMed, 2005, Leuk. Lymphoma, 46(2), pp. 251-231.
Nagao, K. et al., "Effect of MX-68 on airway inflammation and hyperresponsiveness in mice and guinea-pigs". Journal of Pharmacy and Pharmacology, JPP 2004, 56, pp. 187-196.
National Institute of Neurological Disorders, Index Stroke, 2006.
Norman, P. "PDE4 inhibitors". Ashley Publications Ltd., Expert Opinions Ther. Patents, 1999, pp. 1101-1118.
Office Action mailed Dec. 10, 2003 for U.S. Appl. No. 10/226,710, filed Aug. 23, 2002. Inventor: Eckhart Bauer.
Office Action mailed Apr. 28, 2004 for U.S. Appl. No. 10/374,876, filed Feb. 26, 2003. Inventor: Matthias Hoffmann.
Ohio Dept of Health, "Brain and Other Central Nervous System Cancer in Ohio, 1997-2001". Sep. 2004, pp. 1-4.
Organic Chemistry, Grupo Editorial Iberoamerica, Section 13, 3, pp. 301-302, 1983 (best copy available in Spanish).
Rylander, P.N. "Hydrgenation Methods". 1985, Chapter 13.
Rylander, P.N. "Hydrgenation Methods". 1985, Chapters 3, 4.
Rylander, P.N. "Hydrgenation Methods". 1985, Chapters 8, 9, 10, 11.
Rylander, P.N. "Hydrgenation Methods". 1985, Chapter 5, 6, 7.
Rylander, P.N., "Hydrogenation Methods". 1985, Chapters 1, 2.
Santing, R. R E. et al., "Brochodilatory and anti-inflammatory properties of inhaled selective phosphodiesterase inhibitors in a guinea pig model of allergic asthma". European Journal of Pharmacology, 429, 2001, pp. 335-344.
Savelli, F. et al., "Heterotricyclic system Part II—synthesis of new pyrido[12':4,5]pyrazino[3,2-d] pyrimidines". Bollettino Chimico Farmaceutico, 131(8), Sep. 1992, pp. 309-312.

Snyder, J. S. et al., "Common bacteria whose susceptibility to antimicrobials is no longer predictable". NCBI, PubMed, 2000, Le Journal Medical Libanais (The Lebanse Medical Journal), 48, pp. 208-214.

Souillac, P. et al., "Characterization of delivery systems, differential scanning calorimetry". (in Encyclopedia of Controlled Drug Delivery), 1999, John Wiley & Sons, pp. 212-227.

Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21- pp. 129-133.

Takai, N. et al., "Polo-like kinases (PLKs) and cancer". Oncogene, 2005, 24, pp. 287-291.

Tenbrink, R. E. et al., "Antagonist, partial agonist, and full agonist imidazo[1,5-a]quinoxaline amides and carbamates acting through the Baba/Benzodiazepine receptor". J. Med. Chem. 1994, 37, pp. 758-768.

Turner, W.W.et al., "Recent advances in the medicinal chemistry of antifungal agents". Current Pharmacutical Design, 1996, 2, pp. 209-224.

Verschuren, E.W. et al., "The cell cycle and how it is steered by Kaposi's sarcoma-associated herpesvirus cyclin". Journal of General Virology, 2004, 85, pp. 1347-1361.

Vippagunta, S. R. et al., "Crystalline solids". Advanced Drug Delivery Reviews, 48, 2001, pp. 3-26.

Visiting Nurse Association of America. www.vnaa.org/gen/Germ_Protection_Center_Cold_and_Flu_Resources,html, 2009.

* cited by examiner

_US 8,188,086 B2_

SPECIFIC SALT, ANHYDROUS AND CRYSTALLINE FORM OF A DIHYDROPTERIDIONE DERIVATIVE

This application is a continuation of application Ser. No. 11/668,681 filed Jan. 30, 2007.

The present invention relates to a specific salt of a dihydropteridione derivative, namely the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, to its anhydrous form, to its crystallisation in the form of an hydrate with water, to a process for the manufacture thereof, and to the use thereof in a pharmaceutical composition.

BACKGROUND TO THE INVENTION

A number of dihydropteridione derivatives are already known in the prior art. Thus, for example, International Patent Applications WO 03/020722 and WO 2004/076454 disclose dihydropteridione derivatives, a process for their manufacture and their use in a pharmaceutical composition to treat diseases connected with the activity of specific cell cycle kinases and characterised by excessive or abnormal cell proliferation.

The compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide and a process for its manufacturing are specifically disclosed in WO 2004/076454.

However, the above-mentioned patent applications do not disclose any specific salt form or crystal form of any of the compounds exemplified therein.

Although the pharmacologically valuable properties of the dihydropteridinone derivatives disclosed in the art and mentioned above constitute the basic prerequisite for effective use of the compounds as pharmaceutical compositions, an active substance must in any case satisfy additional requirements in order to be accepted for use as a drug. These parameters are largely connected with the physicochemical nature of the active substance. Hence, there continues to be a need for novel salt and crystalline forms of active substances, which can be conveniently formulated for administration to patients and which are pure and highly crystalline in order to fulfil exacting pharmaceutical requirements and specifications.

Preferably, such compounds will be readily formed and have favourable bulk characteristics. Examples of favourable bulk characteristics are drying times, filterability, solubility, intrinsic dissolution rate, stability in general and especially thermal stability, and hygroscopicity.

An absence of breakdown products in the pharmaceutical composition being used is also favourable, since if breakdown products are present in the pharmaceutical composition the content of active substance present in the pharmaceutical formulation might be lower than specified.

Another critical parameter to be controlled is the hygroscopicity, since the absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. In addition, the uptake of moisture may reduce the content of pharmaceutically active substance during manufacture if the pharmaceutical substance is exposed to the environment without being protected from moisture in any way. Preferably, therefore, the hygroscopicity of a pharmaceutically active substance should be well characterised, and possibly also stabilized.

As the crystal modification of an active substance is important to the reproducible active substance content of a preparation, there is a need to clarify as far as possible any existing polymorphism of an active substance present in crystalline form. If there are different polymorphic modifications of an active substance care must be taken to ensure that the crystalline modification of the substance does not change in the pharmaceutical preparation later produced from it. Otherwise, this could have a harmful effect on the reproducible potency of the drug. Against this background, active substances characterised by only slight polymorphism are preferred.

Decreased levels of organic solvents in the crystal lattice are also favourable, due in part to potential solvent toxicity to the recipient as a function of the solvent.

Another criterion which may be of exceptional importance under certain circumstances depending on the choice of formulation or the choice of manufacturing process is the solubility of the active substance. If for example pharmaceutical solutions are prepared (e.g. for infusions) it is essential that the active substance should be sufficiently soluble in physiologically acceptable solvents. For drugs which are to be taken orally, it is in general very important that the active substance should be sufficiently soluble and bioavailable.

Furthermore, the process for preparing such a compound also needs to be conveniently carried out on commercial scale.

Hence, without being restrictive, examples of the parameters which needs to be controlled are the stability of the starting substance under various environmental conditions, the stability during production of the pharmaceutical formulation and the stability in the final compositions of the drug.

The pharmaceutically active substance used to prepare the pharmaceutical compositions should therefore have great stability which is ensured even under all kinds of environmental conditions.

The problem of the present invention is thus to provide a pharmaceutically active substance which is not only characterised by high pharmacological potency but also satisfies the above-mentioned physicochemical requirements as far as possible.

SUMMARY OF THE INVENTION

Surprisingly, it has been found that the problem outlined above is solved by the trihydrochloride salt and by the crystalline trihydrochloride hydrate form of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, the structure of which is depicted below in the form of the free base as formula (I).

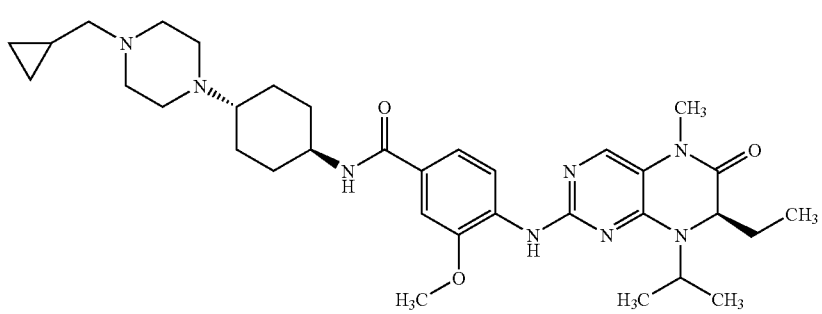

(I)

The trihydrochloride salt and the crystalline trihydrochloride hydrate form of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide offer numerous advantages over the free base and the anhydrous form of this compound. Hence, over the anhydrous form, the crystalline trihydrochloride hydrate form presents for example an advantage of stability under ambient conditions.

Furthermore, when compared to the base salt, the trihydrochloride salt presents an advantage of solubility in water, where the trihydrochloride is much more soluble than the free base.

Lastly, when compared to other common salt form builders, the trihydrochloride salt form presents also advantages as far as the yield, purity and reproducibility of the synthesis of the salt form are concerned.

Thus, a first object of the present invention is the trihydrochloride salt form of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide.

A further object of the present invention is the trihydrochloride anhydrous form of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide.

A further object of the present invention are the crystalline trihydrochloride hydrate forms of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide.

A further object of the present invention is the crystalline trihydrochloride trihydrate form of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide.

A further object of the present invention is an improved process for the manufacturing of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide.

A further object of the present invention is a process for the manufacturing of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide.

A further object of the present invention is a pharmaceutical composition comprising the trihydrochloride salt, a crystalline trihydrochloride hydrate form or the crystalline trihydrochloride trihydrate form of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, together with one or more pharmaceutically acceptable carriers, diluents or excipients.

A further object of the present invention is the use of the trihydrochloride salt, a crystalline trihydrochloride hydrate form or the crystalline trihydrochloride trihydrate form of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, in a method for treating diseases characterised by excessive or abnormal cell proliferation, or for preparing a pharmaceutical composition which is suitable for treating diseases characterised by excessive or abnormal cell proliferation.

DETAILED DESCRIPTION OF THE INVENTION

Figure 1:
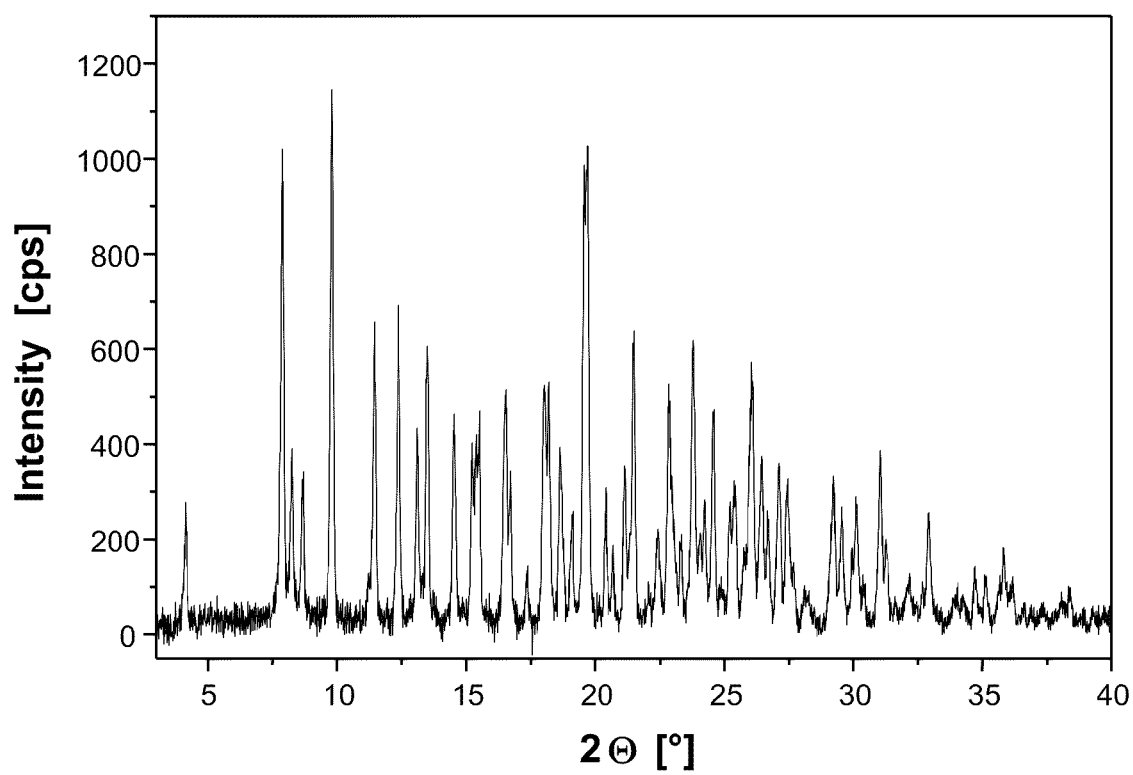
FIG. 1 shows the X-ray powder diffractogram of the crystalline trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, recorded using a Bruker D8 Advanced-diffractometer fitted with a location-sensitive detector (OED) and a Cu anode as the x-ray source (CuK$\alpha$ radiation, $\lambda$=1.54056 Å, 40 kV, 40 mA).

As already mentioned hereinbefore, the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide is specifically disclosed in WO 2004/076454, as well as a process for its preparation. For details on a process to manufacture this compound, reference is thus made to this patent application.

For an alternative process to manufacture this compound, reference is made to the following process.

Abbreviations used.

TLC Thin-Layer Chromatography

DSC Differential Scanning Calorimeter

TG ThermoGravimetry

The starting materials trans-4-aminocyclohexanol 10, 3-methoxy-4-nitrobenzoic acid 2, N-(cyclopropylmethyl) piperazine 12c, and 4-acetamido-cyclohexanone 18 are known compounds which are commercially available.

This process is a convergent process, which includes the steps of:

(i) synthesis of a compound of formula 15c

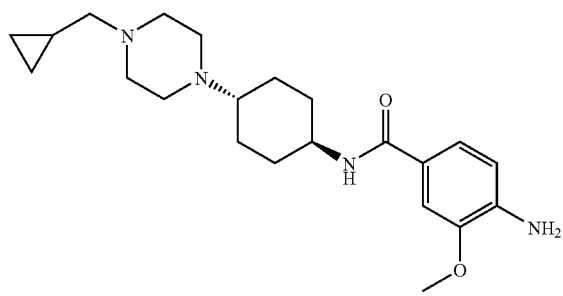

15c (ii) synthesis of a compound of formula 16

16 and (iii) reacting the compound of formula 15c with the compound of formula 16.

In the foregoing, the synthesis of a compound of formula 15c and the synthesis of a compound of formula 16 are described.

(i) Synthesis of a Compound of Formula 15c

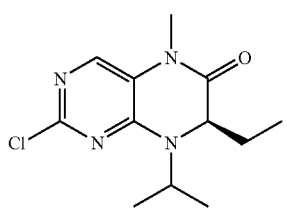

10   2

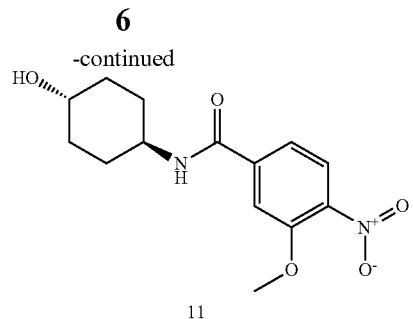

11

260 g (1.32 mol) 3-methoxy-4-nitrobenzoic acid 2 are placed in 1.5 L toluene. 300 mL toluene are distilled off. 5 mL dimethylformamide are added to the residue and 123 mL (1.7 mol) thionyl chloride are added dropwise thereto. The reaction solution is refluxed for 2 hours. The solvent is concentrated by evaporation using the rotary evaporator under reduced pressure. The residue is dissolved in 500 mL tetrahydrofuran and added dropwise to a suspension of 202 g (1.33 mol) trans-4-aminocyclohexanol 10 in 1.5 L tetrahydrofuran and 1.38 L of a 30% potassium carbonate solution, so that the temperature is maintained between 5° and 13° C. The mixture is stirred for 1 hour at 20° C. and 5 L demineralised water are added. The precipitate is suction filtered and washed with demineralised water. The solid is dried at 70° C. in the circulating air dryer. 380 g (98% of theory) product 11 are obtained.

TLC (methylene chloride/ethanol=9:1) $R_f$=0.47

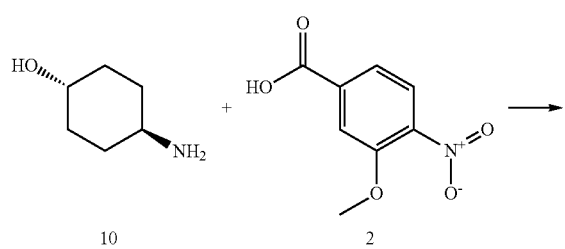

1 g of finely powdered ruthenium(III)-chloride hydrate are added to 185 g (0.63 mol) 11 and 234 g N-methylmorpholine-N-oxide in 1.8 L acetonitrile and the mixture is refluxed for 1 hour. Under reduced pressure 1.6 L acetonitrile are evaporated off. 1.5 L demineralised water are added to the residue and the suspension is cooled to 5° C. The precipitate is suction filtered and washed with plenty of demineralised water. The solid is dried at 70° C. in the circulating air dryer. 168 g (91% of theory) product 13 are obtained.

TLC (methylene chloride/ethanol=9:1) $R_f$=0.64

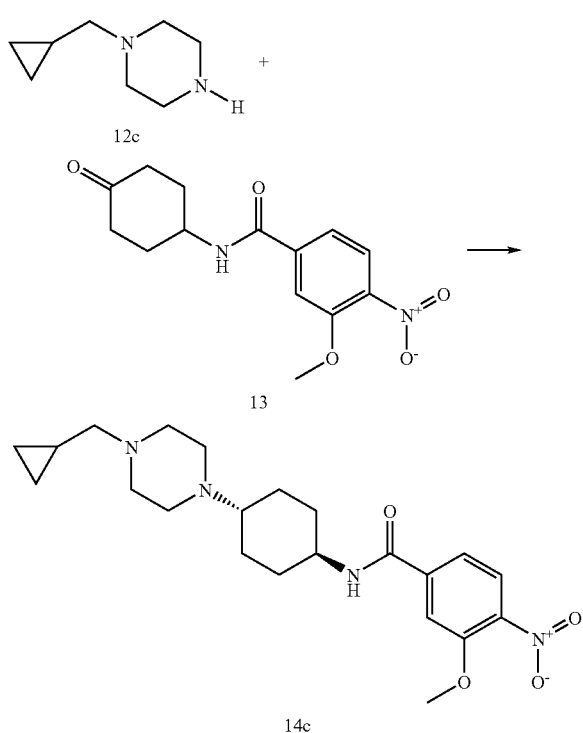

112 g (383 mmol) of product 13, 108 g (770 mmol) N-(cyclopropylmethyl)piperazine 12c and 4.5 mL methanesulphonic acid in toluene are refluxed for 3 hours using the water separator (approx. 76 mL water are separated off). Under reduced pressure 900 mL toluene are evaporated off and the residue is suspended in 1.2 L ethanol. 15 g sodium borohydride are added batchwise to this suspension at a temperature of 15° to 25° C. within one hour. The mixture is stirred for 3 hours at 20° C. and another 4 g sodium borohydride are added. The mixture is stirred for 16 hours at 20° C. Under reduced pressure 650 mL ethanol are evaporated off. 2 L demineralised water and 300 mL cyclohexane are added. The mixture is cooled to 5° C. and the suspension is suction filtered. The residue is dissolved in 1 normal hydrochloric acid. 5 g activated charcoal are added and the mixture is suction filtered. 400 mL tert.-butylmethylether are added to the filtrate and it is made alkaline with ammonia solution. It is cooled to 4° C., the precipitate is suction filtered and washed with demineralised water. The residue is refluxed in 400 mL tert.-butylmethylether. It is cooled, the solid is suction filtered and washed with tert.-butylmethylether. After drying in the circulating air dryer at 60° C. 73 g (46% of theory) product 14c is obtained.

TLC (methylene chloride/ethanol=9:1) $R_f$=0.2

The compound 14c may alternatively also be prepared by the following method.

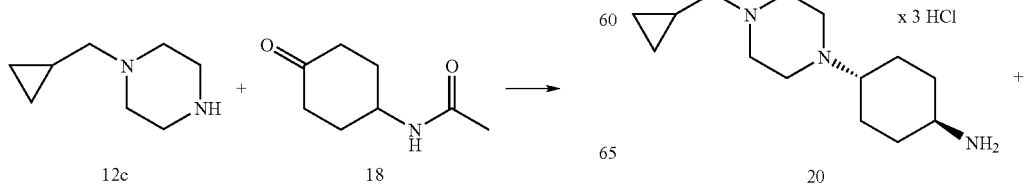

22 g (142 mmol) 4-acetamido-cyclohexanone 18, 39.7 g (283 mmol) N-cyclopropylmethylpiperazine 12c and 0.71 mL methanesulphonic acid in 175 mL toluene are refluxed using the water separator until no more water is precipitated. The mixture is left to cool and at 50° C. 175 mL ethanol are added and the resulting mixture is cooled to 20° C. 5.37 g (142 mmol) sodium borohydride are added batchwise with thorough stirring and the mixture is stirred for 16 hours at 20° C. 200 mL of 4 normal hydrochloric acid are added dropwise to the reaction mixture. Under reduced pressure 200 mL solvent are evaporated off. 100 mL saturated potassium carbonate solution and 200 mL methylisobutylketone are added to the residue. The two-phase mixture is cooled to 5° C. with thorough stirring. The product is suction filtered and dissolved at reflux temperature in 90 mL methylisobutylketone. After the addition of activated charcoal it is filtered hot. The mixture is left to cool and the precipitate is removed by suction filtration. After drying, 16.2 g (41% of theory) of trans compound 19 are obtained.

TLC (methylene chloride/ethanol/ammonia=9:1:0.1) $R_f$=0.39

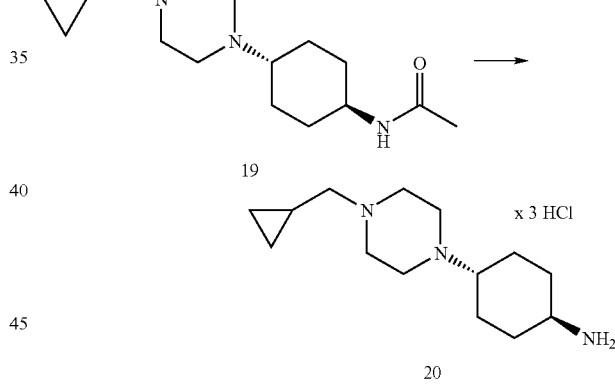

A solution of 44 g (157 mmol) of product 19 in 500 mL 24% hydrochloric acid is refluxed for 6 hours. The solvent is concentrated by evaporation under reduced pressure and the residue is crystallised from 700 mL isopropanol. The precipitate is suction filtered, washed with tert.-butylmethylether and dried at 60° C. in the vacuum drying cupboard. 54.7 g product 20 are obtained as the trihydrochloride (contains 5% water).

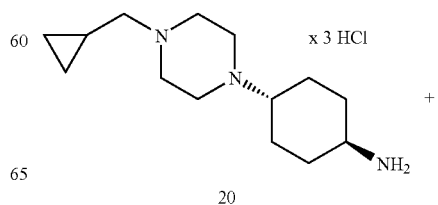

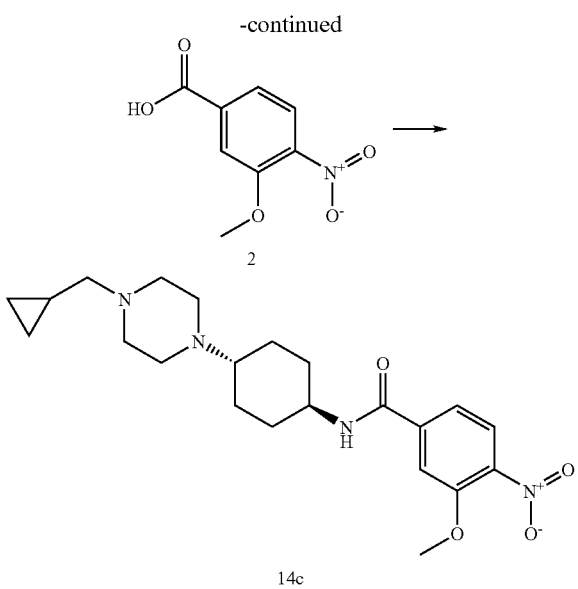

33 g (90.4 mmol) 3-methoxy-4-nitrobenzoic acid 2 are suspended in 80 mL toluene. 0.5 mL dimethylformamide and 16 g (134 mmol) thionyl chloride are added. The mixture is refluxed for 1 hour. The solution is concentrated by evaporation under reduced pressure and the crude acid chloride is dissolved in 50 mL tetrahydrofurane. The solution is added dropwise to a suspension of 18.7 g (94.9 mmol, 95%) of 20 trihydrochloride and 49 g (397 mmol) of diisopropylethylamine in 150 mL tetrahydrofurane while being cooled in the ice bath. TLC is used to check that the reaction is complete. After the reaction has ended water is added to the suspension and the pH is adjusted to 10 by the addition of sodium hydroxide solution. The organic phase is separated off and washed with saturated saline solution. The combined aqueous phases are extracted once with tetrahydrofurane. The combined organic phases are concentrated by evaporation under reduced pressure. The residue is refluxed in 300 mL tert.-butylmethylether. The mixture is left to cool to 20° C. and the precipitate is suction filtered. After drying in the vacuum drying cupboard at 45° C., 31.3 g (83% of theory) of product 14c is obtained.

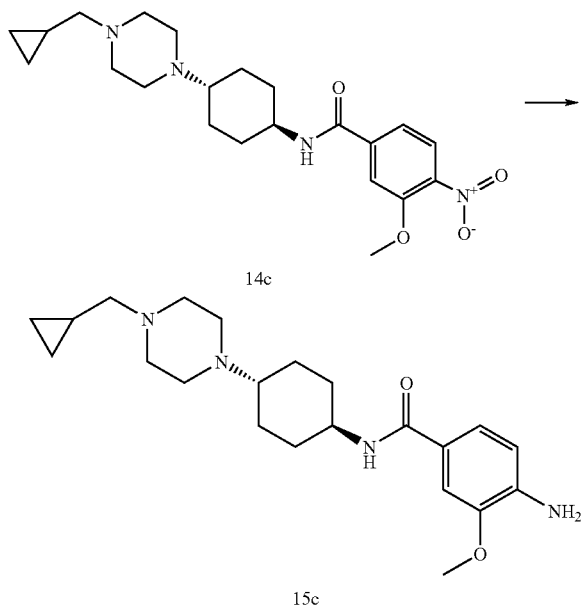

A solution of 72.5 g (174 mmol) of product 14c in 700 mL methanol and 145 mL dimethylformamide is hydrogenated in the presence of 10 g Raney nickel at a temperature of 20° C. and a hydrogen pressure of 50 psi. The catalyst is filtered off and the methanol is evaporated under reduced pressure. 500 mL demineralised water are added to the residue and the suspension is cooled to 5° C. The precipitate is suction filtered and washed with demineralised water. After drying in the circulating air dryer at 60° C., 60.5 g (90% of theory) of product 15c is obtained.

TLC (methylene chloride/ethanol/ammonia=9:1:0.1) $R_f$=0.58

(ii) Synthesis of a Compound of Formula 16

The synthesis of the 2-chloro-7-ethyl-7,8-dihydro-5-methyl-8-(1-methylethyl)-(7R)-6(5H)-pteridinone 16 is described in general in WO 2004/076454, to which reference is made.

The present invention provides an alternative route of synthesis of the 2-chloro-7-ethyl-7,8-dihydro-5-methyl-8-(1-methylethyl)-(7R)-6(5H)-pteridinone 16, which is described in the following.

The following starting materials are known and commercially available: (R)-2-amino-butyric acid 21 and 2,4-dichloro-5-nitropyrimidine 5.

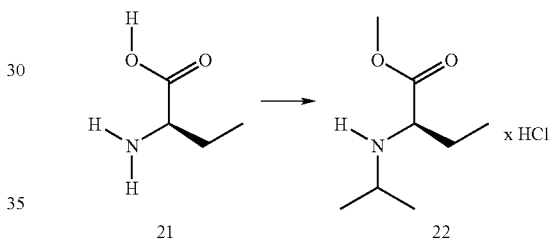

A suspension of 25 g (242 mmol) (R)-2-amino-butyric acid 21 and 32 mL (290 mmol) trimethylorthoformate in 150 mL methanol is heated to 50° C. At this temperature 26.5 mL (364 mmol) of thionylchloride are added in 30 minutes. Under evolution of gas the temperature increases to 60° C. The reaction mixture is refluxed for 3 hours. 125 mL methanol are distilled off and 100 mL toluene are added. 75 mL of solvent are removed by distillation. A suspension of 77 g (364 mmol) sodium triacetoxyborohydride in 175 mL toluene is added to the reaction mixture at 60° C. 22 mL acetone are added at 40° C. The reaction mixture is stirred for 16 hours at room temperature. Under cooling 73 mL ammonia (25%) is added. After addition of 50 mL of demineralised water the mixture is heated to 50° C. The organic phase is separated and washed with demineralised water. 24 mL of a 10 molar solution of hydrogenchloride in ethanol is added. 125 mL of solvent are removed by distillation. 175 mL tetrahydrofurane is added and the suspension is cooled to 2° C. The suspension is suction filtered and washed with cold tetrahydrofurane. After drying in a vacuum drying oven at 50° C., 42.9 g (90% of theory) of product 22 as hydrochloride is obtained.

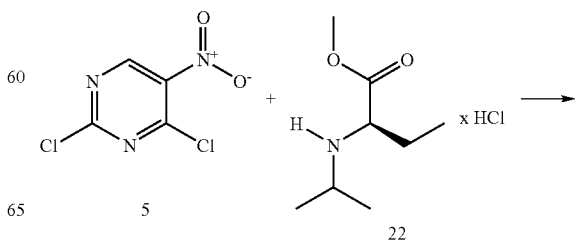

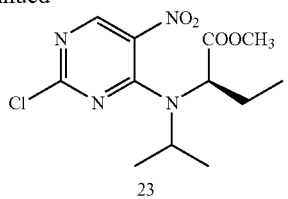

23

9.3 mL of a 50% aqueous sodium hydroxide solution is added to a stirred mixture of 33.3 g (170 mmol) 22 hydrochloride in 60 mL cyclohexane and 60 mL demineralised water. The aqueous phase is separated and the organic phase is added dropwise to a refluxed suspension of 30 g (155 mmol) 5 and 52 g (619 mmol) sodium hydrogencarbonate in 230 mL cyclohexane. The suspension is refluxed for 5 hours using a water separator to remove the formed water. 75 mL of solvent is destined off. At 75° C. the suspension is suction filtered to remove the salts. The solvent is destined of. The residue is dissolved in 240 mL 2-propanol and 90 mL of solvent is destined of again. The solution is cooled slowly to 2° C. The suspension is suction filtered and washed with cold 2-propanol. After drying in a vacuum drying oven at 50° C., 38.9 g (79% of theory) of product 23 is obtained Lipophilic solvents such as e.g. cyclohexane, methylcyclohexane, toluene and the mixtures thereof are particularly suitable for achieving high regioselectivity in the nucleophilic substitution reaction with compound 5.

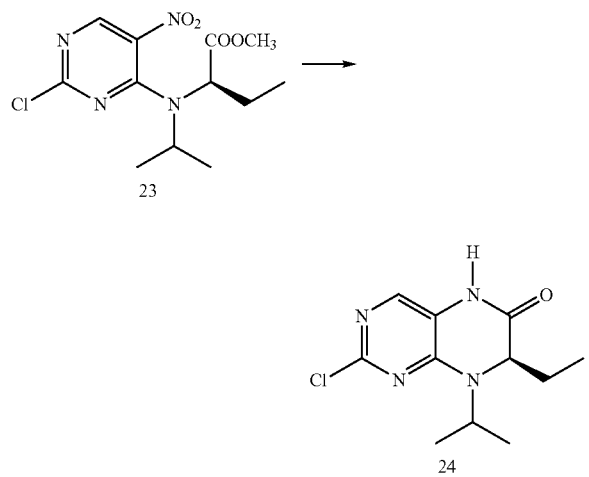

50 g 23 in 375 mL of tetrahydrofurane is hydrogenated in the presence of 5 g Platinum on Carbon (5%) at a hydrogene pressure of 3 bar and at 35° C. until no further hydrogene consumed. 2.5 g vanadyl acetylacetonate are added and the hydrogenation is continued. The suspension is filtered to remove the catalysts. The solvent is removed under reduced pressure. 150 mL 2-propanol are added to the residue and heated to reflux. 300 ml of demineralised water are added. The suspension is cooled slowly to 2° C. The suspension is suction filtered and washed with a cold mixture of 2-propanol and demineralised water. After drying in a vacuum drying oven at 50° C., 36 g (90% of theory) of product 24 is obtained

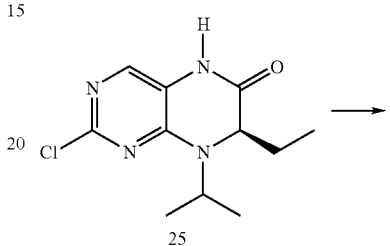

25

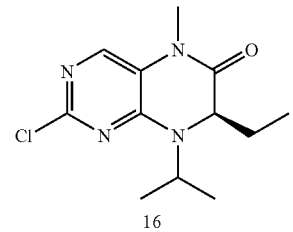

16

A suspension of 7 g (27.5 mmol) of product 25 and 5.7 g (41 mmol) potassium carbonate in 30 mL dimethylcarbonate is heated to 130° C. in an autoclave for 5 hours. The mixture is left to cool and 25 mL demineralised water and 15 mL ethyl acetate are added with stirring. The organic phase is distilled off under reduced pressure. A mixture of 25 mL ethanol and 45 mL demineralised water is added to the residue and heated to 60° C. The solution is left to cool to room temperature. The precipitate is suction filtered and washed with a mixture of demineralised water and ethanol (2:1). The product is dried at 50° C. in the vacuum drying cupboard. 6 g (82% of theory) of product 16 are obtained.

(iii) Reaction of a Compound of Formula 15c with a Compound of Formula 16

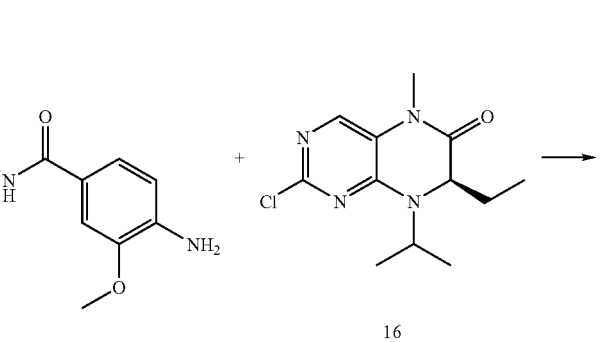

-continued

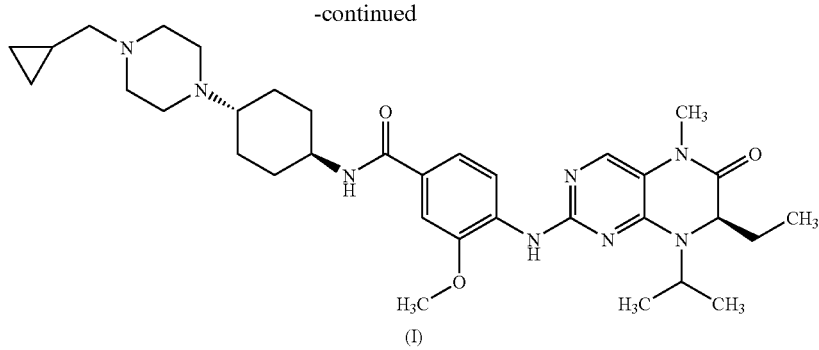
(I)

A solution of 23 g (59.5 mmol) of compound 15c, 16.8 g (62.5 mmol) 2-chloro-7-ethyl-7,8-dihydro-5-methyl-8-(1-methylethyl)-(7R)-6(5H)-pteridinone 16 and 28.3 g (149 mmol) para-toluenesulphonic acid hydrate in 350 mL 2-methyl-4-pentanol is refluxed for 22 hours using the water separator. After the addition of 1 g of compound 16 the mixture is refluxed for a further 2 hours. 300 mL solvent are distilled off and the viscous oil is allowed to cool to 60° C. 300 mL methylene chloride and 300 mL demineralised water are added and the pH is raised by adding approx. 20 mL of 10 normal sodium hydroxide solution to pH=9. The organic phase is washed twice with demineralised water and dried over sodium sulphate. The solvent is evaporated off under reduced pressure and the residue is dissolved at 65° C. in 200 mL ethyl acetate. The mixture is left to cool slowly to 20° C., the precipitate is suction filtered and washed with cold ethyl acetate. After drying at 60° C. in the vacuum drying cupboard 24.4 g (66% of theory) of product (I) is obtained (m.p.=182° C., DSC: 10 K/min, additional endothermic effects in the DSC diagram before melting).

Thus, it is an object of the present invention to provide a process for the manufacture of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I)

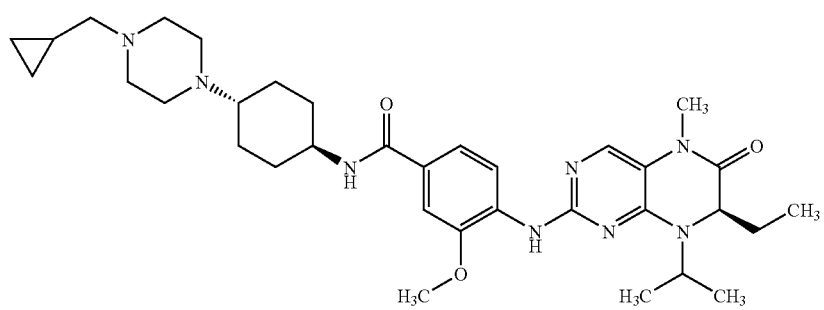
(I)

characterised in that a compound of formula 15c

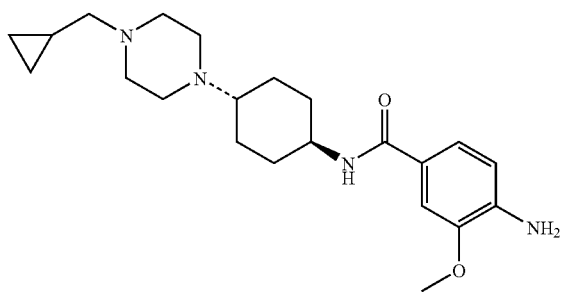
15c is reacted with a compound of formula 16,

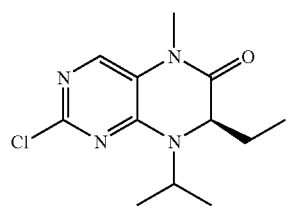
16 wherein the compound of formula 16 is prepared by methylation of a compound of formula 8

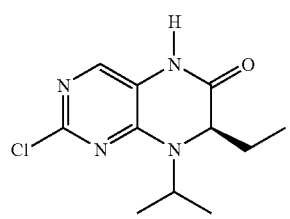
8 in the presence of dimethylcarbonate.

The present invention further provides a process for the manufacture of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I), said process comprising the steps of contacting, under elevated temperature or at room temperature, N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide dissolved in a suitable solvent or in a mixture of solvents, with hydrochloric acid or hydrogen chloride gas dissolved in an organic solvent, optionally in the presence of para-toluenesulfonic acid, and collecting the precipitate formed. Suitable solvents to dissolve N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide for performing the salt formation are alcohols like methanol, ethanol, 1- or 2-propanol, isomeric alcohols of butanol, isomeric alcohols of pentanol, isomeric alcohols of hexanol, like 2-methyl-4-pentanol, ketones like acetone, dialkylethers like tetrahydrofurane, acetic acid esters like ethyl acetate, organic acids like acetic acid, amides like N-methylpyrrolidinone and nitriles like acetonitrile.

An alternative manufacturing process is illustrated by the following experiment, in which the trihydrochloride salt is obtained by addition of concentrated hydrochloric acid to the reaction medium after completion of the acid mediated nucleophilic aromatic substitution reaction of the compound 15c with the compound 16. The following example is illustrative of the present invention and therefore is not to be regarded as a limitation to its scope.

A suspension of 143 g (0.37 mol) 15c and 110 g (0.41 mol) 16 in 2 L 2-methyl-4-pentanol is heated up to 60° C. 176 g (0.93 mol) para-toluenesulfonic acid monohydrate are added and the mixture is heated to reflux for 24 hours using a water separator. The solution is cooled to 100° C. 183 g concentrated hydrochloric acid are added. At 60° C. 1.5 L acetone are added. The suspension is stirred for 16 hours at room temperature. The precipitate is suction filtered and washed with acetone. The product is dried at 60° C. in the vacuum drying cupboard. 267 g (92% of theory) of compound (I) as trihydrochloride are obtained.

A further object of the present invention is the following step of purification of the trihydrochloride salt via crystallization, wherein:
 the compound (I) as trihydrochloride is suspended in a suitable organic solvent, such as ethanol;
 the reaction medium is heated to reflux;
 water is added;
 after cooling the precipitate is collected, washed with a suitable solvent, such as ethanol, and dried.

The following example of purification via crystallization is illustrative of the present invention and therefore is not to be regarded as a limitation to its scope.
 Example of purification of the trihydrochloride salt of the compound of formula (I) via crystallization.

A suspension of 15.5 g of compound (I) as trihydrochloride in 160 mL dry ethanol is heated to reflux. 5.5 mL of demineralised water are added. The solution is left to cool slowly to 20° C. and stirred 16 hours at 20° C. The precipitate is suction filtered and washed with ethanol. After drying at 50° C. in the vacuum drying cupboard 13.3 g (86% of theory) of compound (I) as trihydrochloride is obtained.

A further object of the present invention is a process for the manufacture of an hydrated crystal form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I), said process comprising the steps of:
 dissolving the compound (I) as base in a suitable organic solvent, such as ethanol, at room temperature or elevated temperature;
 adding hydrochloric acid to the reaction medium;
 cooling the reaction medium;
 collecting the precipitate, washing the precipitate with e.g. ethanol, and drying.

The following example of manufacture of an hydrated crystal form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I) is illustrative of the present invention and therefore is not to be regarded as a limitation to its scope.
 Example of manufacture of an hydrated crystal form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I).

1.1 g of concentrated hydrochloric acid are added to a solution of 2 g of the free base of (I) in 30 mL ethanol. After stirring for 2 hours at 20° C. the suspension is cooled to 2° C. The precipitate is suction filtered and washed with ethanol. After drying in the vacuum drying cupboard 2.15 g (91% of theory) of product (I) as trihydrochloride are obtained.

The trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I), is represented by the following Formula.

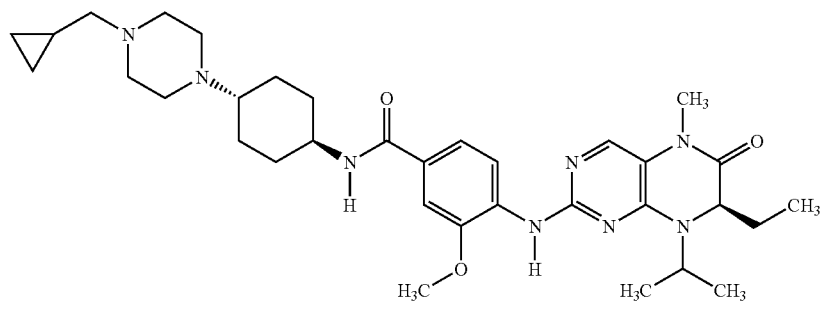

$C_{34}H_{50}N_8O_3 \times 3$ HCl

MW = 728.21

The present invention also provides a process for the manufacture of an anhydrous form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I), wherein a preparation of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I) is dried at a temperature above 130° C. and maintained under dry atmosphere.

The following solubility and solid state characteristics of an hydrated form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I), are relevant to the present invention.

Solubility properties of an hydrated form of the trihydrochloride salt of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide.

Solubility in Aqueous Media

Table I shows the values of solubility of an hydrated form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I) in different aqueous media.

TABLE I

| Medium | Solubility [mg/ml] | pH of the saturated solution |
|---|---|---|
| water | >10 | 3.7 |
| 0.1 N HCl | >10 | 1.3 |
| 0.01 N HCl | >10 | n.d. |
| 0.1 mol/l citric acid | >10 | n.d. |
| 0.1 mol/l tartaric acid | >10 | n.d. |
| 0.01 mol/l methanesulfonic acid | >10 | n.d. |
| McIlvaine buffer pH 2.2 | >10 | 2.3 |
| McIlvaine buffer pH 3.0 | 6.2 | 3.0 |
| McIlvaine buffer pH 4.0 | 7.2 | 3.9 |
| McIlvaine buffer pH 5.0 | 7.2 | 4.7 |
| McIlvaine buffer pH 6.0 | 7.1 | 5.7 |
| McIlvaine buffer pH 7.4 | 7.8 | 7.1 |
| 0.1 mol/l meglumine | 0.017 | pH 8.9 |
| 0.01 N NaOH | >10 | pH 7.4 | n.d. = not determined

From the above results, it can be concluded that this hydrated form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I) has a pH dependent solubility profile in aqueous media with high solubility in acidic and neutral media and strongly reduced solubility in basic media due to the lower solubility of the free base.

Solubility in Organic Media

This hydrated form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I) is highly soluble (>10 mg/ml) in propylenglycol, glycofurol, Cremophor RH40 (30% aqueous solution), Poloxamer 188 (20% aqueous solution), Solutol HS 15 (20% aqueous solution) as well as HP-β-cyclodextrin (20%-, 10%-, 5%-aqueous solutions).

Solid state properties of an hydrated form of the trihydrochloride salt of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide.

Appearance

In the solid state, this hydrated form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I) appears as a white to off-white microcrystalline powder.

Crystallinity and Polymorphism

This hydrated form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I) is highly crystalline. The X-ray powder diffraction diagram is shown in FIG. 1.

The X-ray powder reflection and intensities (standardised) are shown in the following Table II.

TABLE II

| 2Θ [°] | $d_{hkl}$ [Å] | Intensity $I/I_o$ [%] |
|---|---|---|
| 4.13 | 21.38 | 24 |
| 7.88 | 11.21 | 89 |
| 8.25 | 10.71 | 34 |
| 8.66 | 10.21 | 28 |
| 9.81 | 9.01 | 100 |
| 11.45 | 7.73 | 54 |
| 12.38 | 7.14 | 59 |
| 13.12 | 6.74 | 37 |
| 13.50 | 6.55 | 52 |
| 14.53 | 6.09 | 39 |
| 15.26 | 5.80 | 32 |
| 15.40 | 5.75 | 32 |
| 15.51 | 5.71 | 37 |
| 16.52 | 5.36 | 43 |
| 16.71 | 5.30 | 28 |
| 17.35 | 5.11 | 10 |
| 18.04 | 4.91 | 43 |
| 18.19 | 4.87 | 42 |
| 18.65 | 4.75 | 32 |
| 19.10 | 4.64 | 19 |
| 19.56 | 4.53 | 79 |
| 19.64 | 4.52 | 82 |
| 20.40 | 4.35 | 24 |
| 20.69 | 4.29 | 14 |
| 21.15 | 4.20 | 28 |
| 21.49 | 4.13 | 52 |
| 22.07 | 4.02 | 7 |
| 22.42 | 3.96 | 16 |
| 22.86 | 3.89 | 40 |
| 23.33 | 3.81 | 16 |
| 23.81 | 3.73 | 51 |
| 24.08 | 3.69 | 16 |
| 24.25 | 3.67 | 22 |
| 24.57 | 3.62 | 38 |
| 25.24 | 3.53 | 22 |
| 25.40 | 3.50 | 24 |
| 25.78 | 3.45 | 13 |
| 26.08 | 3.41 | 48 |
| 26.45 | 3.37 | 32 |
| 26.70 | 3.34 | 22 |
| 27.12 | 3.29 | 31 |
| 27.45 | 3.25 | 28 |
| 27.68 | 3.22 | 13 |
| 28.13 | 3.17 | 6 |
| 29.24 | 3.05 | 28 |
| 29.56 | 3.02 | 22 |

TABLE II-continued

| 2 Θ [°] | $d_{hkl}$ [Å] | Intensity $I/I_o$ [%] |
|---|---|---|
| 29.94 | 2.98 | 14 |
| 30.12 | 2.96 | 22 |
| 30.39 | 2.94 | 9 |
| 31.04 | 2.88 | 32 |
| 31.29 | 2.86 | 15 |
| 31.64 | 2.83 | 6 |
| 32.16 | 2.78 | 8 |
| 32.69 | 2.74 | 8 |
| 32.92 | 2.72 | 21 |

In Table II above the value "2 Θ [°]" denotes the angle of diffraction in degrees and the value "$d_{hkl}$ [Å]" denotes the specified distances in Å between the lattice planes.

According to the findings shown in Table II the present invention further relates to the crystalline trihydrochloride trihydrate salt form of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, characterised in that in the x-ray powder diagram it has, inter alia, the characteristic values d=3.73 Å, 4.13 Å, 4.52 Å, 4.53 Å, 6.55 Å, 7.14 Å, 7.73 Å, 9.01 Å and 11.21 Å (most prominent peaks in the diagram).

Figure 2:
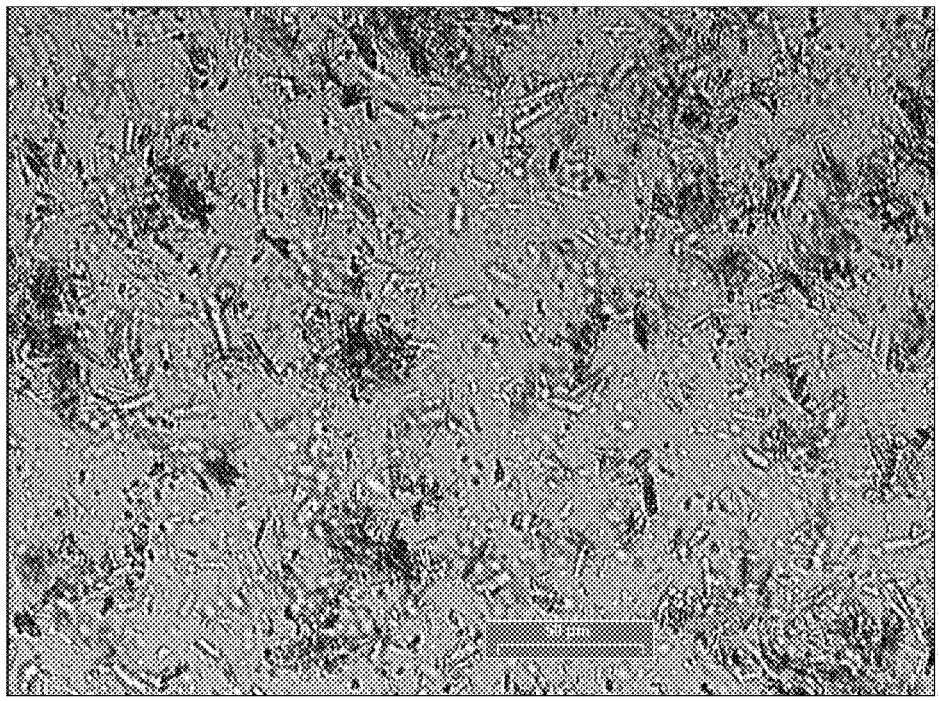
FIG. 2 shows a light microscopy photograph of crystals of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide.

The material crystallizes in rod like crystals, as shown in enclosed FIG. 2.

Under standard conditions the crystalline trihydrochloride salt form of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide according to the invention is present in the form of an hydrate and is obtainable after drying with a changing stoichiometry (1-3 water equivalents). The hydrate with a stoichiometry close to a trihydrate seems to be the stable hydrated form under ambient conditions and can be obtained after conditioning of the dried material. The crystal water is tightly bound. Lowering the humidity down to 10% r.h. does not result in a significant weight loss.

Thus, the present invention further relates to the crystalline trihydrochloride salt of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, characterised in that it is in a trihydrate form.

Figure 3:
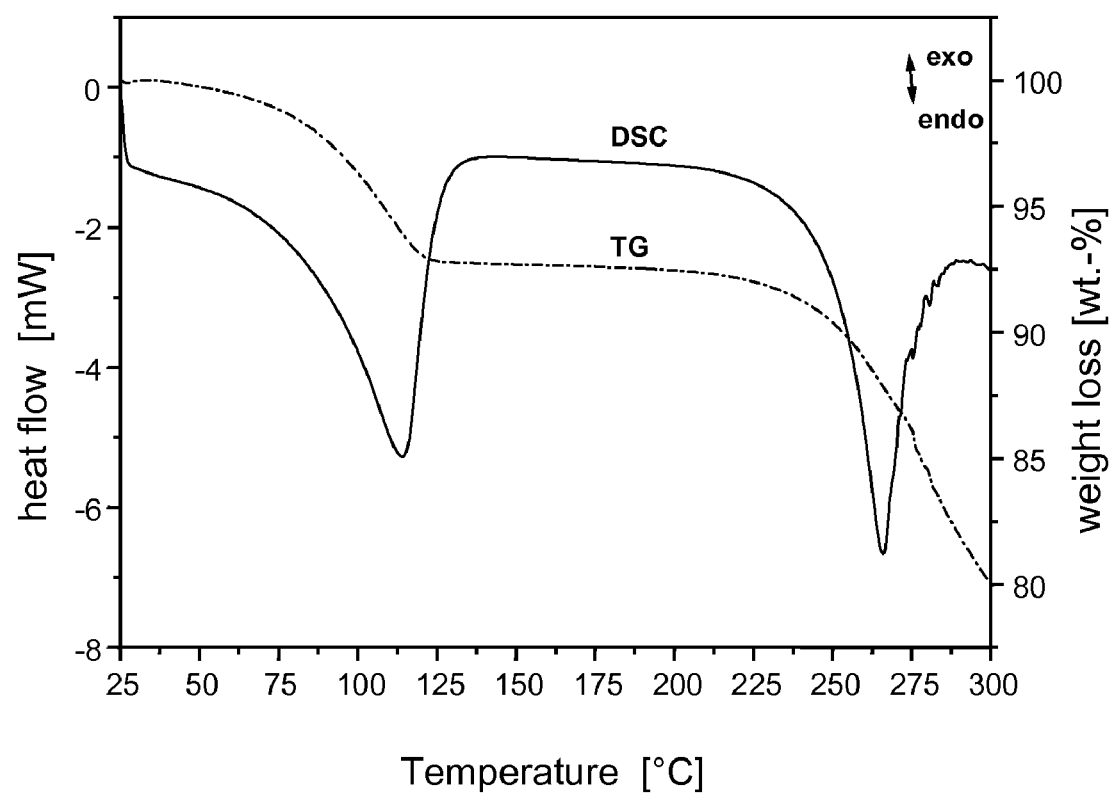
FIG. 3 shows the thermoanalysis and determination of the melting point (DSC/TG) of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, recorded using a DSC and evaluated by the peak onset (heating rate: 10° C./min). The value given is determined using a DSC 821e made by Mettler Toledo.

The thermoanalysis of the crystalline form of the crystalline trihydrochloride salt of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide according to the invention shows a $T_{fus}$=245±5° C. (DSC: 10 K·min$^{-1}$ heating rate), under decomposition, and a broad endothermic effect between 60-140° C., corresponding with the release of water. The DSC/TG diagram is shown in FIG. 3. A closer look to the TG-trace shows a weight loss of approx. 7.5±0.5 wt.-% between 60 and 140° C. This weight loss can be attributed to the release of occluded crystal water.

Correlating the observed weight loss with the molecular weight of the trihydrochloride salt of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide reveals a stoichiometry of the respective hydrated form close to a trihydrate.

$C_{34}H_{50}N_8O_3 \times 3HCl \times 3H_2O$ M=782.26

$-3H_2O \Downarrow \Delta m = -6.9\%$

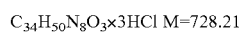

$C_{34}H_{50}N_8O_3 \times 3HCl$ M=728.21

At about 260° C. another strong endothermic peak can be observed in the DSC-diagram, indicating melting of the dehydrated form. The onset of this melting event is at about 245° C. Melting occurs, however, under decomposition, indicated by the accompanied weight loss upon melting. When performing a TG-IR coupling experiment, it can be shown that hydrochloric acid is released upon decomposition. The respective anhydrous form, obtained by heating a sample up to 140° C. is not stable.

Thus, the present invention further relates to the crystalline trihydrochloride salt of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, characterised by a melting point of $T_{m.p.}$=245±5° C. (determined by DSC; evaluation using peak-maximum; heating rate: 10° C./min).

Solid State Stability

When testing the stability of the crystalline trihydrochloride hydrated salt form of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide under harsh stress conditions (24 hours at 105° C., 72 hours at 70° C. and >90% rel. humid., or 24 hours in a Xenotester (λ=300-800 nm, 250 W·m$^{-2}$)), the results show that the trihydrochloride hydrated salt of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide is very stable in the solid state. No significant decomposition or impurities (Σ<2.4%) can be observed under the applied stress conditions.

From the above data, it can be concluded that the hydrated form of the trihydrochloride salt of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I) is characterized by its high solubility in acidic and neutral media and its high crystallinity. The crystalline polymorph form is characterized as a trihydrate. The crystalline form is very stable under harsh stress conditions and is readily soluble in physiologically acceptable solvents. Physiologically acceptable solvents are known to the person skilled in the art and comprise, without limitation, for example isotonic salt or sugar containing solutions such as a 0.9% NaCl solution, a 5% glucose or mannitol solution, or a Ringer/lactate solution.

The present invention also relates to the metabolites of the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide of formula (I), to prodrugs of this compound or of these metabolites obtained via, for example, chemical or non-chemical derivatization of the entire molecule or of one or more chemical groups on the molecule, to conjugates of this compound or of these metabolites with a natural or artificial polymer (for example an oligopeptide, a protein or a chemical polymer), and to the use thereof in a pharmaceutical composition.

"Metabolites" are intended to include compounds which are generated from the active parent drug according to formula (I) or other formulas or compounds of the present invention in vivo when such parent drug is administered to a mammalian subject.

Metabolites provide the same pharmacological effect and include compounds of the present invention wherein for example an alkyl-amino group is replaced by an un-substituted amino group or the corresponding N-oxide, an ester group is replaced by the corresponding carboxylate, or a methyl group has been transformed into a hydroxymethyl or a carboxyl group.

"Prodrugs" are intended to include any covalently bonded carriers which release the active parent drug according to formula (I) or other formulas or compounds of the present invention in vivo when such prodrug is administered to a mammalian subject. Prodrugs of a compound of the present invention, for example the compound of formula (I), are prepared by modifying functional groups present in the compound in such a way that the modifications are cleaved, either in routine manipulation or in vivo, to the parent compound.

"Conjugates" are intended to include any covalently bonded natural or artificial polymer (for example an oligopeptide, a protein or a chemical polymer) which release the active parent drug according to formula (I) or other formulas or compounds of the present invention in vivo when such conjugate is administered to a mammalian subject. Conjugates of a compound of the present invention, for example formula (I), are prepared by attaching functional groups present in the compound to an oligopeptide, a protein or a polymer in such a way that the modifications are cleaved in vivo by a bio-molecule, which usually is found in the vicinity of the target, to the parent compound.

Like the dihydropteridinone derivatives mentioned in WO 2004/076454, the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide also has, in particular, an inhibiting effect on specific cell cycle kinases. Thus, this compound may be used for example to treat diseases connected with the activity of specific cell cycle kinases and characterised by excessive or abnormal cell proliferation, and especially for treating diseases connected with the activity of the polo-like kinase PLK-1. Such diseases include, for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphoma and solid tumours; skin diseases (e.g. psoriasis); bone diseases; cardiovascular diseases (e.g. restenosis and hypertrophy). This compound is also suitable for protecting proliferating cells (e.g. hair, intestinal, blood and progenitor cells) from damage to their DNA caused by radiation, UV treatment and/or cytostatic treatment (Davis et al., 2001). It may be used for the prevention, short-term or long-term treatment of the abovementioned diseases, also in combination with other active substances used for the same indications, e.g. cytostatics.

Furthermore, the compounds in accordance with the present invention may be used on their own or in conjunction with other pharmacologically active substances.

Suitable preparations for the pharmaceutical compositions in accordance with the present invention include for example tablets, capsules, suppositories, solutions,—particularly solutions for injection (s.c., i.v., i.m.) and infusion—elixirs, emulsions or dispersible powders. The proportion of the pharmaceutically active compound(s) should be in the range from 0.01 to 90 wt.-%, preferably 0.1 to 50 wt.-% of the composition as a whole, i.e. in amounts which are sufficient to achieve the dosage necessary to achieve a therapeutic effect. If necessary the doses specified may be given several times a day.

Suitable tablets may be obtained, for example, by mixing the active substance(s) with known excipients, for example inert diluents such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral route, by injection or transdermally. For oral administration the tablets may of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The following examples of formulations illustrate the present invention without restricting its scope.

| A) | Tablets | per tablet |
|---|---|---|
| | active substance | 100 mg |
| | lactose | 140 mg |
| | maize starch | 240 mg |
| | polyvinylpyrrolidone | 15 mg |
| | magnesium stearate | 5 mg |
| | | 500 mg |

The finely ground active substance, lactose and some of the maize starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | lactose | 55 mg |
| | maize starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the maize starch, lactose, microcrystalline cellulose and polyvinylpyrrolidone are mixed together, the mixture is screened and worked with the remaining maize starch and water to form a granulate which is dried and screened. The sodium carboxymethyl starch and the magnesium stearate are added and mixed in and the mixture is compressed to form tablets of a suitable size.

| C) | Ampoule solution | |
|---|---|---|
| | active substance | 50 mg |
| | sodium chloride | 900 mg |
| | sodium hydroxide | up to pH 4.0 |
| | water for inj. | q.s.p. 100 ml |

The active substance is dissolved in water at its own pH and sodium chloride is added to make the solution isotonic. The pH is then adjusted to 4.0 by addition of sodium hydroxide 1N. The resulting solution is filtered to remove pyrogens and the filtrate is transferred under aseptic conditions into ampoules which are then sterilised and heat-sealed. The ampoules may contain 5 mg, 25 mg or 50 mg of active substance.

The invention claimed is:

1. A crystalline, hydrated form of the trihydrochloride salt of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide wherein the hydrated form is mono-, di- or trihydrate or mixtures thereof.

2. A crystalline, hydrated form of the trihydrochloride salt of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, wherein the hydrate contains up to three water molar equivalents.

3. A pharmaceutical composition comprising the crystalline compound in accordance with claim 1, together with a pharmaceutically acceptable carrier or diluent.

4. The crystalline hydrated form of the trihydrochloride salt of N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide, having the following characteristic values d: 3.73 Å, 4.13 Å, 4.52 Å, 4.53 Å, 6.55 Å, 7.14 Å, 7.73 Å, 9.01 Å and 11.21 Å wherein the x-ray source is CuKα radiation, λ=1.54056 Å, 40 kV, 40 mA.

5. A pharmaceutical composition comprising the crystalline compound in accordance with claim 4, together with a pharmaceutically acceptable carrier or diluent.

\* \* \* \* \*